United States Patent
Kim et al.

(10) Patent No.: US 11,407,848 B2
(45) Date of Patent: Aug. 9, 2022

(54) METHOD FOR PREPARING SUPER ABSORBENT POLYMER

(71) Applicant: LG Chem, Ltd., Seoul (KR)

(72) Inventors: Moo Kon Kim, Daejeon (KR); Sang Gi Lee, Daejeon (KR); Hye Mi Nam, Daejeon (KR); Chang Hun Lee, Daejeon (KR); Tae Yun Kim, Daejeon (KR)

(73) Assignee: LG Chem, Ltd.

( * ) Notice: Subject to any disclaimer, the term of this patent is extended or adjusted under 35 U.S.C. 154(b) by 503 days.

(21) Appl. No.: 16/474,850

(22) PCT Filed: Oct. 15, 2018

(86) PCT No.: PCT/KR2018/012127
§ 371 (c)(1),
(2) Date: Jun. 28, 2019

(87) PCT Pub. No.: WO2019/083211
PCT Pub. Date: May 2, 2019

(65) Prior Publication Data
US 2019/0344242 A1 Nov. 14, 2019

(30) Foreign Application Priority Data

Oct. 27, 2017 (KR) .................. 10-2017-0141504
Oct. 12, 2018 (KR) .................. 10-2018-0121994

(51) Int. Cl.
| | | |
|---|---|---|
| *C08F 222/10* | (2006.01) | |
| *B01J 20/26* | (2006.01) | |
| *B01J 20/28* | (2006.01) | |
| *B01J 20/30* | (2006.01) | |
| *C08F 220/06* | (2006.01) | |
| *C08J 3/24* | (2006.01) | |

(52) U.S. Cl.
CPC ......... *C08F 222/102* (2020.02); *B01J 20/267* (2013.01); *B01J 20/28004* (2013.01); *B01J 20/28011* (2013.01); *B01J 20/28016* (2013.01); *B01J 20/3021* (2013.01); *B01J 20/3085* (2013.01); *C08F 220/06* (2013.01); *C08J 3/245* (2013.01); *C08F 222/1063* (2020.02); *C08F 2810/20* (2013.01)

(58) Field of Classification Search
CPC ................ C08F 222/102; C08F 220/06; C08F 222/1063; C08F 2810/20; C08F 2/26; C08F 6/008; C08F 20/06; C08F 2/44; B01J 20/267; B01J 20/28004; B01J 20/28011; B01J 20/28016; B01J 20/3021; B01J 20/3085; C08J 3/245; C08J 2333/02; C08J 2205/02; C08J 2300/14; A61L 15/60

See application file for complete search history.

(56) References Cited

U.S. PATENT DOCUMENTS

| | | | |
|---|---|---|---|
| 4,883,478 A | 11/1989 | Lerailler et al. | |
| 5,342,899 A * | 8/1994 | Graham | A61L 15/60 264/37.28 |
| 5,455,284 A | 10/1995 | Dahmen et al. | |
| 6,107,358 A * | 8/2000 | Harada | C08F 2/10 521/133 |
| 6,174,929 B1 | 1/2001 | Hahnle et al. | |
| 2006/0276598 A1 | 12/2006 | Wada et al. | |
| 2010/0099781 A1* | 4/2010 | Tian | C08F 265/06 521/40.5 |
| 2012/0258851 A1* | 10/2012 | Nakatsuru | A61L 15/48 502/7 |
| 2013/0101851 A1 | 4/2013 | Takaai et al. | |
| 2014/0031473 A1 | 1/2014 | Nogi et al. | |
| 2016/0271584 A1 | 9/2016 | Lee et al. | |
| 2016/0367965 A1 | 12/2016 | Kim et al. | |

(Continued)

FOREIGN PATENT DOCUMENTS

| | | |
|---|---|---|
| CN | 102712712 A | 10/2012 |
| DE | 4021847 A1 | 1/1992 |

(Continued)

OTHER PUBLICATIONS

Chinese Search Report for Application No. 201880012410.4 dated Jul. 21, 2021, pp. 1-2.
Buchholz et al., "Modern Superabsorbent Polymer Technology", Polymer Science & Technology General, John Wiley & Sons, Inc., Jan. 1998, pp. 69-103.
Third Party Observation for Application No. EP 18871353.1 dated Mar. 3, 2020.
Third Party Observation for Application No. PCT/KR2018/012127 submitted Feb. 19, 2020.
Extended European Search Report including the Written Opinion for Application No. 18871353.1 dated Nov. 27, 2019, 7 pages.
International Search Report for PCT/KR2018/012127 dated Jan. 29, 2019.

(Continued)

*Primary Examiner* — Robert C Boyle
(74) *Attorney, Agent, or Firm* — Lerner, David, Littenberg, Krumholz & Mentlik, LLP

(57) ABSTRACT

A method is provided for preparing a super absorbent polymer capable of exhibiting an excellent absorption rate by including a uniform porous structure through a simple and economical process. The method includes: performing a crosslinking polymerization of a water-soluble ethylenically unsaturated monomer to form a hydrogel polymer; drying and pulverizing the hydrogel polymer; classifying the pulverized polymer into polymer particles having a particle size of at least 10 to 150 μm, polymer particles having a particle size of 150 to 200 μm, and polymer particles having a particle size of 200 to 850 μm to form a base polymer powder having a particle size of 150 to 850 μm; and surface-crosslinking the base polymer powder, wherein in the crosslinking polymerization step, the foaming polymerization proceeds in the presence of polymer particles having an average particle size of 10 to 200 μm obtained in the classifying step and an anionic surfactant.

8 Claims, No Drawings

(56) References Cited

U.S. PATENT DOCUMENTS

| | | |
|---|---|---|
| 2017/0014801 A1 | 1/2017 | Ikeuchi et al. |
| 2017/0095792 A1 | 4/2017 | Kim et al. |
| 2017/0166707 A1 | 6/2017 | Jang et al. |
| 2017/0216816 A1 | 8/2017 | Matsumoto et al. |
| 2017/0216817 A1 | 8/2017 | Torii et al. |
| 2018/0037686 A1 | 2/2018 | Lee et al. |
| 2018/0050321 A1 | 2/2018 | Lee et al. |
| 2018/0194904 A1 | 7/2018 | Lee et al. |
| 2018/0257059 A1 | 9/2018 | Heo et al. |

FOREIGN PATENT DOCUMENTS

| | | |
|---|---|---|
| EP | 1837348 A1 | 9/2007 |
| EP | 2518092 A1 | 10/2012 |
| EP | 2589613 A1 | 5/2013 |
| EP | 3248991 A1 | 11/2017 |
| EP | 3424989 A1 | 1/2019 |
| JP | 2005126474 A | 5/2005 |
| JP | 2015120933 A | 7/2015 |
| JP | 2016540106 A | 12/2016 |
| KR | 20060009316 A | 1/2006 |
| KR | 20110087293 A | 8/2011 |
| KR | 20120132475 A | 12/2012 |
| KR | 20150059626 A | 6/2015 |
| KR | 20150068322 A | 6/2015 |
| KR | 20160074204 A | 6/2016 |
| KR | 101672564 B1 | 11/2016 |
| KR | 20160127742 A | 11/2016 |
| KR | 20160128319 A | 11/2016 |
| KR | 20160144902 A | 12/2016 |
| KR | 20170057705 A | 5/2017 |
| KR | 20170075643 A | 7/2017 |
| KR | 20170100395 A | 9/2017 |
| WO | 8703208 A1 | 6/1987 |
| WO | 9201008 A1 | 1/1992 |
| WO | 9220723 A1 | 11/1992 |
| WO | 2011078298 A1 | 6/2011 |
| WO | 2014095633 A1 | 6/2014 |
| WO | 2016052537 A1 | 4/2016 |
| WO | 2017026623 A1 | 2/2017 |

OTHER PUBLICATIONS

Odian, "Principles of Polymerization", Second Edition, A Wiley-Interscience Publication, 1981, p. 203.

Schwalm, "UV Coatings: Basics, Recent Developments and New Applications", Elsevier Science, Dec. 2006, p. 115.

\* cited by examiner

METHOD FOR PREPARING SUPER ABSORBENT POLYMER

CROSS-REFERENCE TO RELATED APPLICATIONS

This application is a national phase entry under 35 U.S.C. § 371 of International Application No. PCT/KR2018/012127 filed Oct. 15, 2018, which claims priority to Korean Patent Application No. 10-2017-01451504, filed Oct. 27, 2017, and Korean Patent Application No. 10-2018-0121994, filed Oct. 12, 2018, the disclosures of which are incorporated herein by reference.

TECHNICAL FIELD

The present invention relates to a method for preparing a super absorbent polymer which enables production of a super absorbent polymer capable of exhibiting an excellent absorption rate by including a uniform porous structure through a simple and economical process.

BACKGROUND

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like. Such super absorbent polymers started to be practically applied in sanitary products, and now they are widely used for preparation of hygiene products such as paper diapers for children or sanitary napkins, water retaining soil products for gardening, water stop materials for the civil engineering and construction, sheets for raising seedling, fresh-keeping agents for food distribution fields, materials for poultice or the like.

In most cases, these super absorbent polymers have been widely used in the field of hygienic materials such as diapers or sanitary napkins. In such hygienic materials, the super absorbent polymer is generally contained in a state of being spread in the pulp. In recent years, however, continuous efforts have been made to provide hygienic materials such as diapers having a thinner thickness. As a part of such efforts, the development of so-called pulpless diapers and the like in which the content of pulp is reduced or pulp is not used at all is being actively advanced.

As described above, in the case of hygienic materials in which the pulp content is reduced or the pulp is not used, a super absorbent polymer is contained at a relatively high ratio and these super absorbent polymer particles are inevitably contained in multiple layers in the hygienic materials. In order for the whole super absorbent polymer particles contained in the multiple layers to absorb liquid such as urine more efficiently, it is necessary for the super absorbent polymer to basically exhibit high absorption performance and absorption rate.

Thus, in recent years, attempts have been made to prepare and provide a super absorbent polymer exhibiting a more enhanced higher absorption rate. In order to produce a super absorbent polymer exhibiting a high absorption rate in this way, it is necessary to prepare a super absorbent polymer containing a porous structure through foaming or the like. Previously, for the introduction of such a porous structure, a method of applying a foaming agent and/or a surfactant during polymerization has been typically used.

However, when a super absorbent polymer is produced through polymerization by using a foaming agent and/or a surfactant that has been previously used, there is a disadvantage that it is difficult to introduce uniform porous structure, the absorption rate is insufficient and the absorption rate becomes very uneven for each particle.

Therefore, a method of applying a special additive such as a capsule-type foaming agent has recently been attempted. However, since such capsule-type foaming agent and the like are very expensive compared with the unit price of the super absorbent polymer itself, there were the disadvantages that the economy efficiency of the entire process is lowered and the process applied thereto is also relatively complicated.

Technical Problem

The present invention provides a super absorbent polymer which enables production of a super absorbent polymer capable of exhibiting an excellent absorption rate by including a uniform porous structure through a simple and economical process without using a special additive.

Technical Solution

According to one embodiment of the present invention, there is provided a method for preparing a super absorbent polymer including the steps of:

performing a crosslinking polymerization of a water-soluble ethylenically unsaturated monomer having an acidic group of which at least a part is neutralized in the presence of an internal crosslinking agent to form a hydrogel polymer containing a first crosslinked polymer;

drying and pulverizing the hydrogel polymer;

classifying the pulverized polymer into polymer particles having a particle size of at least 10 to 150 μm, polymer particles having a particle size of 150 to 200 μm, and polymer particles having a particle size of 200 to 850 μm to form a base polymer powder having a particle size of 150 to 850 μm; and surface-crosslinking the base polymer powder, wherein in the crosslinking polymerization step, the foaming polymerization proceeds in the presence of a polymer particles having average particle size of 10 to 200 μm obtained in the classifying step and an anionic surfactant.

Hereinafter, a method for preparing a super absorbent polymer according to specific embodiments of the present invention will be described in more detail.

In the preparation method of one embodiment described above, the fine powder obtained in the classifying step, that is, polymer particles having a particle size of 10 to 200 μm are used as a kind of foaming agent during the crosslinking polymerization for producing a super absorbent resin, and additionally, anionic surfactants are used as a kind of foam stabilizer. As the foaming polymerization proceeds using such fine powder and anionic surfactant, uniform pores corresponding to the particle size of the fine powder are stably formed in the base polymer powder and the super absorbent polymer obtained through the crosslinking polymerization and the subsequent steps.

As such, according to the method of one embodiment, as a super absorbent polymer having a uniform porous structure, compared to prior arts using a foaming agent or the like, is produced, the super absorbent polymer can exhibit a more enhanced absorption rate, and furthermore, disadvantages of the prior arts, such as nonuniform absorption rate for each particle, are solved, and the super absorbent polymer particles can exhibit an uniform absorption rate as a whole.

Further, in the method of one embodiment, a super absorbent resin having a porous structure stably introduced therein is obtained using a fine powder commonly obtained in the process of preparation of the super absorbent polymer, particularly the classifying step, and a general anionic surfactant, without applying an expensive additive such as a capsule-type foaming agent or a separate process. Thereby, the overall process unit cost of the super absorbent polymer can be greatly reduced, and a super absorbent polymer having an excellent absorption rate can be obtained through a simplified process.

Hereinafter, a method for preparing the super absorbent polymer of one embodiment and a super absorbent polymer obtained thereby will be described in more detail.

First, in the preparation method of one embodiment, the water-soluble ethylenically unsaturated monomer constituting the first crosslinked polymer may be any monomer commonly used for the preparation of the super absorbent polymer. As a non-limiting example, the water-soluble ethylenically unsaturated monomer may be a compound represented by the following Chemical Formula 1:

—COOM$^1$       [Chemical Formula 1]

in Chemical Formula 1, $R_1$ is an alkyl group having 2 to 5 carbon atoms containing an unsaturated bond, $M^1$ is a hydrogen atom, a monovalent or divalent metal, an ammonium group or an organic amine salt.

Preferably, the monomer may be one or more selected from the group consisting of (meth)acrylic acid, and monovalent (alkali) metal salts, divalent metal salts, ammonium salts, and organic amine salts of these acids. When a (meth)acrylic acid and/or a salt thereof is used as the water-soluble ethylenically unsaturated monomer in this way, it is advantageous in that a super absorbent polymer having improved water absorptivity can be obtained. In addition, as the monomer, maleic anhydride, fumaric acid, crotonic acid, itaconic acid, 2-acryloyl ethane sulfonic acid, 2-methacryloyl ethane sulfonic acid, 2-(meth)acryloyl propane sulfonic acid, or 2-(meth)acrylamide-2-methylpropane sulfonic acid, (meth)acrylamide, N-substituted (meth)acrylate, 2-hydroxyethyl(meth)acrylate, 2-hydroxypropyl(meth)acrylate, methoxypolyethyleneglycol(meth)acrylate, polyethyleneglycol(meth)acrylate, (N,N)-dimethylaminoethyl (meth)acrylate, (N,N)-dimethylaminopropyl(meth)acrylamide, and the like may be used.

Here, the water-soluble ethylenically unsaturated monomers may have an acidic group, in which at least a part of the acidic group may be neutralized. Preferably, those in which the monomer is partially neutralized with an alkaline substance such as sodium hydroxide, potassium hydroxide, ammonium hydroxide or the like can be used.

In this case, a degree of neutralization of the monomer may be 55 to 95 mol %, or 60 to 80 mol %, or 65 to 75 mol %. The range of the degree of neutralization may vary depending on the final physical properties. However, an excessively high degree of neutralization causes the neutralized monomers to be precipitated, and thus polymerization may not readily occur, whereas an excessively low degree of neutralization not only greatly deteriorates the absorbency of the polymer, but also endows the polymer with hard-to-handle properties, like elastic rubber.

In the first step of the method of one embodiment, a monomer composition containing a water-soluble ethylenically unsaturated monomer having an acidic group of which at least a part is neutralized as described above can be cross-linked together with an internal crosslinking agent, a polymer particle (fine powder) having an average particle size of 10 to 200 µm or 10 to 150 µm obtained in a classifying process described later, and an anionic surfactant.

In this case, the water-soluble ethylenically unsaturated monomer is as previously described. In addition, the concentration of the water-soluble ethylenically unsaturated monomer in the monomer composition may be appropriately controlled considering the polymerization time and reaction conditions, and so on, and preferably, it may be 20 to 90% by weight, or 40 to 65% by weight. Such a concentration range may be advantageous for controlling of pulverization efficiency when pulverizing polymer as described below, without a need to remove non-reacted monomers after polymerizing using a gel effect appeared in the polymerization reaction of an aqueous solution of high concentration. However, when the concentration of the monomers becomes too low, the yield of the super absorbent polymer may decrease. Conversely, when the concentration of the monomer is excessively high, it may lead to problems in the processes, for example, a part of the monomer may be precipitated, or the pulverization efficiency may be lowered during pulverization of the polymerized hydrogel polymer, etc., and the physical properties of the super absorbent polymer may be deteriorated.

Further, the internal crosslinking agent is not particularly limited as long as it enables the introduction of cross-link when polymerizing the water-soluble ethylenically unsaturated monomer. As non-limiting examples, as the internal crosslinking agent, multifunctional crosslinking agents such as N,N'-methylenebisacrylamide, trimethylolpropane tri(meth)acrylate, ethylene glycol di(meth)acrylate, polyethylene glycol (meth)acrylate, propylene glycol di(meth)acrylate, polypropylene glycol (meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaetythritol pentaacrylate, glycerin tri(meth)acrylate, pentaerythritol tetraacrylate, triarylamine, ethylene glycol diglycidyl ether, propylene glycol, glycerin, or ethylene carbonate may be used alone or in combinations of two or more kinds thereof, but not limited thereto.

The internal crosslinking agent may be added in the concentration of about 0.001 to 1 wt %, based on the monomer composition. That is, when the concentration of the internal crosslinking agent is too low, the absorption speed of super absorbent polymer may decrease and gel strength may weaken. Conversely, when the concentration of the internal crosslinking agent is too high, the absorption power of the super absorbent polymer may decrease, which may be not preferable as an absorber.

Further, in the crosslinking polymerization step, the polymer particles having a particle size of 10 to 200 µm or 10 to 150 µm may be contained in an amount of 0.1 to 5 parts by weight, or 0.5 to 3 parts by weight, or 0.7 to 2.5 parts by weight, based on 100 parts by weight of the monomer. Thus, a uniform porous structure corresponding to the particle size of the polymer particles, i.e., the fine powder, can be introduced into the base polymer powder and the super absorbent polymer, and also the crosslinking polymerization is appropriately performed. Thereby, a super absorbent polymer exhibiting a uniform and improved absorption rate together with excellent physical properties can be obtained.

In addition, in the crosslinking polymerization step, as anionic surfactant, one or more selected from the group consisting of sodium dodecyl sulfate, ammonium lauryl sulfate, sodium laureth sulfate, dioctyl sodium sulfosuccinate, perfluorooctane sulfonate, perfluorobutane sulfonate, alkyl-aryl ether phosphate, alkyl ether phosphate, sodium myreth sulfate and carboxylate salt may be used. In addition, various anionic surfactants may be used. Such anionic surfactant enables the porous structure to be formed better through the foaming polymerization using the fine powder, and can stabilize such a porous structure. Thus, by the additional use of such anionic surfactants, the super absorbent polymer can exhibit a more enhanced absorption rate.

Such anionic surfactant may be used in an amount of 0.002 to 0.05 parts by weight, or 0.005 to 0.02 parts by weight, based on 100 parts by weight of the monomer. Thereby, it is possible to obtain a super absorbent polymer in which a uniform porous structure is properly introduced to exhibit a more enhanced absorption rate and the deterioration of other physical properties is suppressed.

On the other hand, the monomer composition, for example, a monomer aqueous solution may contain one or more additives selected from the group consisting of a polyvalent metal salt, a photoinitiator, a thermal initiator, and a polyalkylene glycol-based polymer, in addition to the monomer, the internal crosslinking agent, the polymer particles having a particle size of 10 to 200 μm and the anionic surfactant.

Such an additive can be used in order to further improve the liquid permeability or the like of the super absorbent polymer (polyvalent metal salt or polyalkylene glycol-based polymer, etc.), or to facilitate the crosslinking polymerization, thus improving the physical properties of the super absorbent polymer.

The above-described additives may be used in an amount of 2000 ppmw or less, or 0 to 2000 ppmw, or 10 to 1000 ppmw, or 50 to 500 ppmw, based on 100 parts by weight of the monomer, depending on their respective roles. As a result, physical properties such as liquid permeability or absorption performance of the super absorbent polymer can be further improved.

As the polyalkylene glycol-based polymer among the above-described additives, polyethylene glycol, polypropylene glycol, and the like may be used.

In addition, as the photo (polymerization) initiator and/or the thermal (polymerization) initiator, any polymerization initiator generally used in the production of a super absorbent polymer may be used. In particular, even though the photo-polymerization is performed, a certain amount of heat may be generated by UV irradiation, etc., and also a certain amount of heat may be generated with the progress of polymerization reaction which is an exothermic reaction. Therefore, the photo (polymerization) initiator and/or the thermal (polymerization) initiator may be used together to produce a super absorbent polymer having a more enhanced absorption rate and various physical properties.

As the thermal (polymerization) initiator, one or more compounds selected from the group consisting of a persulfate-based initiator, an azo-based initiator, hydrogen peroxide, and ascorbic acid may be used. Specific examples of the persulfate-based initiator may include sodium persulfate ($Na_2S_2O_8$), potassium persulfate ($K_2S_2O_8$), ammonium persulfate ($(NH_4)_2S_2O_8$), and the like. Further, examples of the azo-based initiator may include 2,2-azobis-(2-amidinopropane)dihydrochloride, 2,2-azobis-(N,N-dimethylene)isobutyramidine dihydrochloride, 2-(carbamoylazo)isobutylonitrile, 2,2-azobis[2-(2-imidazolin-2-yl)propane] dihydrochloride, 4,4-azobis-(4-cyanovaleric acid) and the like. More various thermal polymerization initiators are well disclosed in "Principle of Polymerization" written by Odian, (Wiley, 1981), p 203, which may be incorporated herein by reference.

As the photo (polymerization) initiator, for example, one or more compounds selected from the group consisting of benzoin ether, dialkyl acetophenone, hydroxyl alkylketone, phenyl glyoxylate, benzyl dimethyl ketal, acyl phosphine, and alpha-aminoketone may be used. Among them, as the specific example of acyl phosphine, commercially available Lucirin TPO, namely, 2,4,6-trimethyl-benzoyl-trimethyl phosphine oxide may be used. More various photo-polymerization initiators are well disclosed in "UV Coatings: Basics, Recent Developments and New Application (Elsevier, 2007)" written by Reinhold Schwalm, p 115, which may be incorporated herein by reference.

Such polymerization initiator may be added at a concentration of 500 ppmw or less with respect to 100 parts by weight of the monomer. That is, if the concentration of the polymerization initiator is too low, the polymerization rate becomes low and thus a large amount of residual monomers may be extracted from the final product, which is not preferable. On the contrary, if the concentration of the polymerization initiator is too high, a polymer chain making up a network may become short, and thus, the physical properties of polymer may be degraded such as increase in the content of water-soluble components and decrease in absorbency under pressure, which is not preferable.

Meanwhile, in addition to the above-described components, the monomer composition may further contain additives such as a thickener, a plasticizer, a preservation stabilizer, and an antioxidant, if necessary.

Further, the monomer composition may be prepared in the form of a solution in which the raw materials such as the above-mentioned monomers are dissolved in a solvent. In this case, as the usable solvent, any solvent may be used without limitations in the constitution, as long as it is able to dissolve the above raw materials. Example of the solvent that can be used include water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, N,N-dimethylacetamide, or a mixture thereof.

And, the monomer composition having the form of the above-described aqueous solution or the like can be controlled so that the initial temperature has a temperature of 30 to 60° C., and light energy or heat energy may be applied thereto to perform crosslinking polymerization.

The formation of hydrogel polymer through crosslinking polymerization of the monomer composition can be carried out by a conventional polymerization method, and the process is not particularly limited. As a non-limiting example, the polymerization process may be largely classified into a thermal polymerization and a photo-polymerization depending on the kind of a polymerization energy source. The thermal polymerization may be performed in a reactor like a kneader equipped with agitating spindles, and the photo-polymerization can be carried out in a reactor equipped with a movable conveyor belt.

As an example, the monomer composition is injected into a reactor like a kneader equipped with the agitating spindles, and thermal polymerization is performed by providing hot air thereto or heating the reactor, to thereby obtain the hydrogel polymer. In this case, the hydrogel polymer, which is discharged from the outlet of the reactor according to the type of agitating spindles equipped in the reactor, can be obtained into a particle having several millimeters to several centimeters. Specifically, the resulting hydrogel polymer may be obtained in various forms according to the concentration of the monomer mixture injected thereto, the injection speed, or the like, and a hydrogel polymer having a (weight average) particle size of 2 to 50 mm may be generally obtained.

As another example, when the photo-polymerization of the monomer composition is carried out in a reactor equipped with a movable conveyor belt, the hydrogel polymer in the form of a sheet may be obtained. In this case, the thickness of the sheet may vary according to the concentration of the monomer composition injected thereto and the injection speed. Usually, the sheet is preferably controlled to have a thickness of 0.5 cm to 5 cm in order to uniformly polymerize the entire sheet and also secure production speed.

The hydrogel polymer obtained by the above-mentioned method may have a water content of 40 to 80% by weight. Meanwhile, the "water content" as used herein means a weight occupied by moisture with respect to a total amount of the hydrogel polymer, which may be the value obtained by subtracting the weight of the dried polymer from the weight of the hydrogel polymer. Specifically, the water content is defined as a value calculated by measuring the weight loss due to evaporation of water in the polymer during the drying process of increasing the temperature of the polymer with infrared heating. At this time, the water content is measured under the drying conditions determined as follows: the drying temperature is increased from room temperature to about 180° C., and then the temperature is maintained at 180° C., and the total drying time is set as 20 minutes, including 5 minutes for the temperature rising step.

On the other hand, after the hydrogel polymer is prepared by the above-mentioned method, a step of drying and pulverizing the hydrogel polymer may be carried out. Prior to such drying, a step of coarsely pulverizing the hydrogel polymer to prepare a hydrogel polymer having a small average particle size may be carried out first.

In this coarsely pulverizing step, the hydrogel polymer can be pulverized into a size of 1.0 mm to 2.0 mm.

A pulverizing device used during the coarse pulverization is not limited by its configuration, and specific examples thereof may include any one selected from the group consisting of a vertical pulverizer, a turbo cutter, a turbo grinder, a rotary cutter mill, a cutter mill, a disc mill, a shred crusher, a crusher, a chopper, and a disc cutter. However, it is not limited to the above-described examples.

Further, for the efficiency of the coarse pulverization, the coarse pulverization can be performed in multiple cycles according to the particle size. For example, the hydrogel polymer may be subjected to primary crude pulverization into an average particle size of about 10 mm, which is again subjected to secondary coarse pulverization into an average particle size of about 5 mm, and then to third coarse pulverization into the above-mentioned particle size.

On the other hand, after the selective coarse pulverization, the hydrogel polymer can be dried. This drying temperature may be 50 to 250° C. When the drying temperature is lower than 50° C., there is a concern that the drying time becomes excessively long or the physical properties of the super absorbent polymer finally formed may be deteriorated, and when the drying temperature is higher than 250° C., only the surface of the polymer is excessively dried, and thus there is a concern that fine powder may be generated and the physical properties of the super absorbent polymer finally formed may be deteriorated. The drying may be more preferably performed at a temperature of 150 to 200° C., and more preferably 160 to 190° C. Meanwhile, the drying may be carried out for 20 minutes to 15 hours, in consideration of the process efficiency, but is not limited thereto.

The drying method may be selected and used in the drying step without limitation in the constitution as long as it may be generally used in the process of drying the hydrogel polymer. Specifically, the drying step may be carried out by a method of supplying hot air, irradiating infrared rays, irradiating microwaves, irradiating ultraviolet rays, or the like. When the drying step as above is finished, the water content of the polymer may be about 0.05 to about 10% by weight.

Next, the dried polymer obtained from the drying step is subjected to a (finely) pulverizing step.

The polymer powder obtained from the pulverization step may have a particle size of 150 to 850 μm. Specific examples of a pulverizing device that may be used to achieve the above particle size may include a ball mill, a pin mill, a hammer mill, a screw mill, a roll mill, a disc mill, a jog mill, or the like, but are not limited to the above-described examples.

In order to manage the physical properties of the super absorbent polymer powder finally commercialized after the pulverization step, a classifying step may be performed according to the particle size of the polymer powder obtained after pulverization.

In particular, in the method of one embodiment, the pulverized polymer can be classified into polymer particles having a particle size of at least 10 to 150 μm, polymer particles having a particle size of 150 to 200 μm, and polymer particles having a particle size of 200 to 850 μm. Of the polymer particles having different particle sizes thus obtained, all of the polymer particles having a particle size of 10 to 150 μm, and optionally a part of the polymer particles having a particle diameter of 150 to 200 μm are taken, and the fine powders containing them are recycled to the above-mentioned cross-linking polymerization step, which can be used as a kind of foaming agent. Thus, as already mentioned above, a super absorbent polymer having a uniform porous structure and a further improved and uniform absorption rate can be provided.

Further, the remaining polymer particles other than these fine particles, for example, the remainder of the polymer particles having a particle size of 150 to 200 μm and all of the polymer particles having a particle size of 200 to 850 μm can be taken to form a base polymer powder having a particle size of 150 to 850 μm.

This classifying step can be carried out using a standard sieve according to a general method of classifying a super absorbent polymer.

The super absorbent polymer can be commercialized through a surface crosslinking reaction step which is described later for the base resin powder having such a particle size, that is, a particle size of 150 to 850 μm, On the other hand, after proceeding the classifying step described above, the super absorbent polymer can be produced through a step of crosslinking the surface of the base resin powder, that is, by subjecting the base polymer powder to heat treatment and crosslinking polymerization in the presence of a surface crosslinking agent containing a surface crosslinking agent.

Here, the kind of the surface crosslinking agent included in the surface crosslinking solution is not particularly limited. Non-limiting examples of the surface crosslinking agent may include one or more compounds selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene carbonate, ethylene glycol, diethylene glycol, propylene glycol, triethylene glycol, tetraethylene glycol, propanediol, dipropylene glycol, polypropylene glycol, glycerin, polyglycerin, butanediol, heptanediol, hexanediol trimethylol propane, pentaerythritol, sorbitol, calcium hydroxide, magnesium hydroxide, aluminum hydroxide, iron hydroxide, calcium chloride, magnesium chloride, aluminum chloride, and iron chloride.

In this case, the content of the surface crosslinking agent may be properly controlled according to the kind of the crosslinking agent or reaction conditions, and the content is preferably 0.001 to 5 parts by weight, based on 100 parts by weight of the base polymer powder. When the content of the surface crosslinking agent is too low, surface crosslinking may hardly occur to deteriorate physical properties of the final super absorbent polymer. On the contrary, when the surface crosslinking agent is excessively used, excessive surface crosslinking reaction may occur, leading to deterioration in absorption capacity of the super absorbent polymer, which is not preferable.

Further, the surface crosslinking solution may further include one or more solvents selected from the group consisting of water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate and N,N-dimethylacetamide. The solvent may be contained in an amount of 0.5 to 10 parts by weight based on 100 parts by weight of the base polymer.

Further, the surface crosslinking solution may further include a thickener. When the surface of the base polymer powder is further crosslinked in the presence of the thickener in this way, deterioration of the physical properties may be minimized even after pulverization. Specifically, one or more selected from polysaccharides and polymers containing hydroxyl groups may be used as the thickener. The polysaccharides may be gum-based thickeners and cellulose-based thickeners. Specific examples of the gum-based thickeners may include xanthan gum, arabic gum, karaya gum, tragacanth gum, ghatti gum, guar gum, locust bean gum, psyllium seed gum, etc., and specific examples of the cellulose-based thickeners may include hydroxypropylmethylcellulose, carboxymethylcellulose, methylcellulose, hydroxymethylcellulose, hydroxyethylcellulose, hydroxypropylcellulose, hydroxyethylmethylcellulose, hydroxymethylpropylcellulose, hydroxyethylhydroxypropylcellulose, ethylhydroxyethylcellulose, methylhydroxypropylcellulose, and the like. Meanwhile, specific examples of the polymers containing hydroxyl groups may include polyethylene glycol, polyvinyl alcohol, and the like.

On the other hand, in order to perform the surface crosslinking, a method of placing the surface crosslinking solution and the base polymer powder into a reaction tank and mixing them, a method of spraying a surface crosslinking solution onto the base polymer powder, a method in which the base polymer powder and the surface crosslinking solution are continuously supplied in a continuously operating mixer and mixed, or the like can be used.

The surface crosslinking may be carried out at a temperature of 100 to 250° C., and it may be continuously performed after the drying and pulverization step which is carried out at a relatively high temperature. At this time, the surface crosslinking reaction may be performed for 1 to 120 minutes, or 1 to 100 minutes, or 10 to 60 minutes. That is, the surface crosslinking reaction may be carried out under the above-mentioned surface crosslinking reaction conditions in order to prevent the polymer particles from being damaged due to excessive reaction while inducing the minimum surface crosslinking reaction.

In the super absorbent polymer prepared as described above, as a uniform porous structure is introduced, the bulk density may be 0.55 to 0.65 g/ml, or 0.57 to 0.64 g/ml. The absorption rate measured according to Vortex measurement method may be 30 to 53 seconds, or 33 to 50 seconds, or 35 to 48 seconds, which show an improved absorption rate. The absorption rate refers the time required for the vortex of the liquid to disappear due to fast absorption when the super absorbent polymer is added to a physiological saline solution and stirred. This can define a fast absorption rate of the super absorbent polymer. The measurement method thereof will be more specified in Examples described later.

Further, the super absorbent polymer may exhibit the features that the centrifuge retention capacity (CRC) measured according to EDANA recommended test method No. WSP 241.3 is 28 to 35 g/g, or 30 to 33 g/g, and the absorbency under load (AUL) at 0.9 psi measured according to EDANA recommended test method No. WSP 242.3 is 16 to 23 g/g, or 17 to 20 g/g. In this manner, the super absorbent polymer can maintain excellent centrifuge retention capacity/absorbency under load while exhibiting an improved absorption rate as described above.

Further, preferably, the super absorbent polymer has an average particle size of 300 to 600 μm. Further, preferably, the super absorbent polymer according to the present invention contains 45 to 85% by weight of a super absorbent polymer having a particle size of 300 to 600 μm. Further, preferably, the super absorbent polymer contains 15% by weight or more of a super absorbent polymer having a particle size of 300 μm.

Advantageous Effects

As described above, according to the present invention, it is possible to prepare a super absorbent polymer capable of exhibiting excellent and wholly uniform absorption rate by including a uniform porous structure through a simple and economical process without using a special additive such as a capsule-type foaming agent.

DETAILED DESCRIPTION OF THE EMBODIMENTS

Hereinafter, preferred examples are provided for better understanding of the invention. However, these Examples are given for illustrative purposes only and are not intended to limit the scope of the present invention thereto.

Example 1

(Step 1)

9 g (80 ppmw with respect to a monomer composition) of 0.5% IRGACURE 819 initiator diluted with acrylic acid and 40 g of 5% polyethylene glycol diacrylate (PEGDA, Mw=400) diluted with acrylic acid were mixed to prepare a solution (solution A).

Into a 2 L-volume glass reactor surrounded by a jacket in which a heating medium pre-cooled to 25° C. was circulated, 490 g of acrylic acid and the solution A were injected. To the glass reactor, 850 g of 24% caustic soda solution (solution C) was slowly added dropwise and mixed. After confirming that the temperature of the mixed solution increased to about 72° C. or higher by neutralization heat, the mixed solution was left until it was cooled. A neutralization degree of acrylic acid in the mixed solution thus obtained was about 70 mol %. 5 g (1 wt % relative to acrylic acid) of the fine powder (polymer particles of the base polymer powder having a particle size of 10 to 150 μm) obtained in step 3 described later was added to the monomer aqueous solution. Further, 5 g (170 ppmw) of 2% sodium dodecylsulfate solution (solution D-1) diluted with water was prepared as a surfactant. Further, 30 g of 4% sodium persulfate solution (solution D-2) diluted with water was prepared. When the temperature of the mixed solution was cooled to about 45° C., the solutions D-1 and D-2 previously prepared were poured into the mixed solution and mixed.

(Step 2)

Then, the mixed solution prepared in step 1 was poured in a Vat-type tray (15 cm in width×15 cm in length) installed in a square polymerizer which had a light irradiation device installed at the top and was preheated to 80° C., and the mixed solution was then subjected to light irradiation. It was confirmed that at about 20 seconds after light irradiation, gel was generated from the surface, and at about 30 seconds after light irradiation, polymerization reaction occurred concurrently with foaming. Then, the polymerization reaction was performed for additional 2 minutes, and the polymerized sheet was taken and cut in a size of 3 cm×3 cm, and then subjected to a chopping process using a meat chopper to prepare the cut sheet as crumbs. The average particle size of the prepared crump was 1.5 mm.

(Step 3)

Subsequently, the crumbs prepared in step 2 were dried in an oven capable of shifting airflow up and down. The crumbs were uniformly dried by flowing hot air at 180° C. from the bottom to the top for 15 minutes and from the top to the bottom for 15 minutes such that the dried crumbs had a water content of about 2% or less. The dried crumbs were pulverized using a pulverizer and classified by size to obtain a base polymer having a size of 150 to 850 μm. The remaining polymer particles of the base polymer powder having a particle size of 10 to 150 μm were recycled to step 1 described above and used.

(Step 4)

Thereafter, 100 g of the base polymer prepared in step 3 was mixed with a crosslinking agent solution which was prepared by mixing 4 g of water, 1 g of ethylene carbonate, and 0.1 g of Aerosil 200 (EVONIK), and then surface crosslinking reaction was performed at 190° C. for 30 minutes. The resulting product was pulverized and then passed through a sieve to obtain a surface-crosslinked super absorbent polymer having a particle size of 150 to 850 μm. 0.1 g of Aerosil 200 was added by a dry process to the obtained super absorbent polymer and mixed in a dry state to prepare a super absorbent polymer.

Example 2

(Step 1)

9 g (80 ppmw with respect to a monomer composition) of 0.5% IRGACURE 819 initiator diluted with acrylic acid and 40 g of 5% polyethylene glycol diacrylate (PEGDA, Mw=400) diluted with acrylic acid were mixed to prepare a solution (solution A).

Into a 2 L-volume glass reactor surrounded by a jacket in which a heating medium pre-cooled to 25° C. was circulated, 490 g of acrylic acid and the solution A were injected. To the glass reactor, 850 g of 24% caustic soda solution (solution C) was slowly added dropwise and mixed. After confirming that the temperature of the mixed solution increased to about 72° C. or higher by neutralization heat, the mixed solution was left until it was cooled. A neutralization degree of acrylic acid in the mixed solution thus obtained was about 70 mol %. 15 g (3 wt % relative to acrylic acid) of the fine powder (polymer particles of the base polymer powder having a particle size of 10 to 150 μm) obtained in step 3 described later was added to the monomer aqueous solution. Further, 5 g (170 ppmw) of 2% sodium dodecylsulfate solution (solution D-1) diluted with water was prepared as a surfactant. Further, 30 g of 4% sodium persulfate solution (solution D-2) diluted with water was prepared. When the temperature of the mixed solution was cooled to about 45° C., the solutions D-1 and D-2 previously prepared were poured into the mixed solution and mixed.

Subsequently, steps 2 to 4 were carried out in the same manner as in Example 1 to prepare a super absorbent polymer.

Example 3

(Step 1)

9 g (80 ppmw with respect to a monomer composition) of 0.5% IRGACURE 819 initiator diluted with acrylic acid and 40 g of 5% polyethylene glycol diacrylate (PEGDA, Mw=400) diluted with acrylic acid were mixed to prepare a solution (solution A).

Into a 2 L-volume glass reactor surrounded by a jacket in which a heating medium pre-cooled to 25° C. was circulated, 490 g of acrylic acid and the solution A were injected. To the glass reactor, 850 g of 24% caustic soda solution (solution C) was slowly added dropwise and mixed. After confirming that the temperature of the mixed solution increased to about 72° C. or higher by neutralization heat, the mixed solution was left until it was cooled. A neutralization degree of acrylic acid in the mixed solution thus obtained was about 70 mol %. 25 g (5 wt % relative to acrylic acid) of the fine powder (polymer particles of the base polymer powder having a particle size of 10 to 150 μm) obtained in step 3 described later was added to the monomer aqueous solution. Further, 5 g (170 ppmw) of 2% sodium dodecylsulfate solution (solution D-1) diluted with water was prepared as a surfactant. Further, 30 g of 4% sodium persulfate solution (solution D-2) diluted with water was prepared. When the temperature of the mixed solution was cooled to about 45° C., the solutions D-1 and D-2 previously prepared were poured into the mixed solution and mixed.

Subsequently, steps 2 to 4 were carried out in the same manner as in Example 1 to prepare a super absorbent polymer.

Comparative Example 1

(Step 1)

9 g (about 80 ppmw with respect to a monomer composition) of 0.5% IRGACURE 819 initiator diluted with acrylic acid and 40 g of 5% polyethylene glycol diacrylate (PEGDA, Mw=400) diluted with acrylic acid were mixed to prepare a solution (solution A).

Into a 2 L-volume glass reactor surrounded by a jacket in which a heating medium pre-cooled to 25° C. was circulated, 490 g of acrylic acid and the solution A were injected. To the glass reactor, 850 g of 24% caustic soda solution (solution C) was slowly added dropwise and mixed. After confirming that the temperature of the mixed solution increased to about 72° C. or higher by neutralization heat, the mixed solution was left until it was cooled. A neutralization degree of acrylic acid in the mixed solution thus obtained was about 70 mol %. 5 g (170 ppmw) of 2% sodium dodecylsulfate solution (solution D-1) diluted with water was prepared as a surfactant. Further, 30 g of 4% sodium persulfate solution (solution D-2) diluted with water was prepared. When the temperature of the mixed solution was cooled to about 45° C., the solutions D-1 and D-2 previously prepared were poured into the mixed solution and mixed. Then, an SBC solution was prepared at a concentration of 4 wt %, and about 6.25 g (500 ppm with respect to the monomer composition) was injected into the mixed solution and mixed.

Subsequently, steps 2 to 4 were carried out in the same manner as in Example 1 to prepare a super absorbent polymer.

Comparative Example 2

A super absorbent polymer was prepared in the same manner as in Example 1 except that sodium dodecylsulfate solution (solution D-1) was not used in step 1.

Comparative Example 3

A super absorbent polymer was prepared in the same manner as in Example 2 except that sodium dodecylsulfate solution (solution D-1) was not used in step 1.

Experimental Example: Evaluation of Physical Properties of Super Absorbent Polymer The physical properties of the super absorbent polymers prepared in Examples and Comparative Examples were measured and evaluated by the following methods, and the results are shown in Table 1 below.

(1) Bulk Density

About 100 g of the super absorbent polymer was added to a funnel-shaped bulk density tester and flowed down in a 100 ml container, and then the weight of the super absorbent polymer contained in the container was measured. The bulk density was calculated as (weight of super absorbent polymer)/(volume of container, 100 ml). (Unit: g/ml).

(2) Absorption Rate (Vortex Time)

The absorption rates of the super absorbent polymers of Examples and Comparative Examples were measured in seconds in accordance with a method described in International Patent Publication WO 1987/003208.

In detail, the absorption rate (or vortex time) was calculated by measuring in seconds the time required for the vortex to disappear, after adding 2 g of the super absorbent polymer to 50 mL of a physiological saline solution at 23° C. to 24° C. and then stirring it a magnetic bar (diameter 8 mm, length 31.8 mm) at 600 rpm.

(3) Centrifuge Retention Capacity (CRC)

The centrifuge retention capacity (CRC) by water absorption capacity under a non-loading condition was measured for each polymer according to EDANA (European Disposables and Nonwovens Association) recommended test method No. WSP 241.3.

In detail, in the polymers respectively obtained through Examples and Comparative Examples, a polymer classified with a 30-50 mesh sieve was obtained. $W_0$ (g) (about 0.2 g) of these polymers were uniformly put in a nonwoven fabric-made bag, followed by sealing. Then, the bag was immersed in a physiological saline solution composed of an aqueous sodium chloride solution (0.9 wt %) at room temperature. After 30 minutes, water was removed from the bag by centrifugation at 250 G for 3 minutes, and the weight $W_2$ (g) of the bag was then measured. Further, the same procedure was carried out without using the polymer, and then the resultant weight $W_1$ (g) was measured.

Using the respective weights thus obtained, CRC (g/g) was calculated according to the following Equation.

$$CRC\ (g/g) = \{[W_2\ (g) - W_1\ (g)]/W_0\ (g)\} - 1 \quad [\text{Equation 1}]$$

(4) Absorbency Under Load (AUL)

Absorbency under load (AUL) at 0.9 psi was measured for each polymer according to EDANA test method WSP 242.3.

First, at the time of measuring the absorbency under load, a polymer classified at the time of CRC measurement was used.

In detail, a 400 mesh stainless steel screen net was installed in the bottom of a plastic cylinder having an internal diameter of 25 mm. $W_0$ (g) (0.16 g) of the super absorbent polymer was uniformly scattered on the steel net at room temperature and humidity of 50%, and a piston which can uniformly provide a load of 0.9 psi was put thereon, in which an external diameter of the piston was slightly smaller than 25 mm, there was no gab between the internal wall of the cylinder and the piston, and the jig-jog of the cylinder was not interrupted. At this time, the weight $W_3$ (g) of the device was measured.

After putting a glass filter having a diameter of 90 mm and a thickness of 5 mm in a petri dish having a diameter of 150 mm, a physiological saline solution composed of 0.9 wt % of sodium chloride was poured in the dish until the surface level became equal to the upper surface of the glass filter. A sheet of filter paper having a diameter of 90 mm was put thereon. The measuring device was put on the filter paper and the solution was absorbed for 1 hour under the load. After 1 hour, the weight $W_4$ (g) was measured after lifting up the measuring device.

The weights thus obtained were used to calculate absorbency under load (g/g) according to the following Equation 2:

$$AUL\ (g/g) = [W_4\ (g) - W_3\ (g)]/W_0\ (g) \quad [\text{Equation 2}]$$

The results measured as above are shown in Table 1 below.

TABLE 1

|  | Bulk density (g/ml) | Vortex (sec) | (#30-50) CRC (g/g) | (#30-50) 0.9 AUL (g/g) |
| --- | --- | --- | --- | --- |
| Example 1 | 0.62 | 41 | 30.4 | 18.3 |
| Example 2 | 0.60 | 37 | 30.1 | 18.5 |

TABLE 1-continued

| | Bulk density (g/ml) | Vortex (sec) | (#30-50) CRC (g/g) | (#30-50) 0.9 AUL (g/g) |
|---|---|---|---|---|
| Example 3 | 0.59 | 55 | 30.5 | 18.7 |
| Comparative Example 1 | 0.61 | 47 | 30.3 | 18.7 |
| Comparative Example 2 | 0.63 | 52 | 30.5 | 18.6 |
| Comparative Example 3 | 0.62 | 51 | 30.3 | 18.6 |

Referring to Table 1 above, it was confirmed that the super absorbent polymers of Examples exhibited excellent absorption rate as compared with Comparative Examples.

The invention claimed is:

1. A method for preparing a super absorbent polymer comprising:
performing a crosslinking polymerization of a water-soluble ethylenically unsaturated monomer having an acidic group of which at least a part is neutralized in the presence of an internal crosslinking agent to form a hydrogel polymer containing a first crosslinked polymer;
drying and pulverizing the hydrogel polymer to form a pulverized polymer;
classifying the pulverized polymer into polymer particles having a particle size of 10 to 150 µm, polymer particles having a particle size of 150 to 200 µm, and polymer particles having a particle size of 200 to 850 µm and combining the polymer particles having a particle size of 200 to 850 µm with at least a portion of the polymer particles having a particle size of 150 to 200 µm to form a base polymer powder having a particle size of 150 to 850 µm; and
surface-crosslinking the base polymer powder,
wherein the crosslinking polymerization is a foaming polymerization which proceeds in the presence of the polymer particles having a particle size of 10 to 150 µm obtained in the classifying step and an anionic surfactant without using a further foaming agent,
wherein the polymer particles having a particle size of 10 to 150 µm is used in an amount of 0.1 to 3 parts by weight based on 100 parts by weight of the monomer, and
wherein the super absorbent polymer has a bulk density of 0.55 to 0.65 g/ml, and an absorption rate measured according to Vortex measurement method of 30 to 53 seconds.

2. The method for preparing a super absorbent polymer according to claim 1, wherein the water-soluble ethylenically unsaturated monomer comprises: a methacrylic acid of which a part is neutralized, and an alkali metal salt thereof; and has a degree of neutralization of 55 to 95 mol %.

3. The method for preparing a super absorbent polymer according to claim 1, wherein the anionic surfactant includes one or more of sodium dodecyl sulfate, ammonium lauryl sulfate, sodium laureth sulfate, dioctyl sodium sulfosuccinate, perfluorooctane sulfonate, perfluorobutane sulfonate, alkyl-aryl ether phosphate, alkyl ether phosphate, sodium myreth sulfate or carboxylate salt.

4. The method for preparing a super absorbent polymer according to claim 1, wherein the anionic surfactant is used in an amount of 0.002 to 0.05 parts by weight, based on 100 parts by weight of the water-soluble ethylenically unsaturated monomer.

5. The method for preparing a super absorbent polymer according to claim 1, wherein during the crosslinking polymerization, a monomer aqueous solution containing the water-soluble ethylenically unsaturated monomer, the internal crosslinking agent, the polymer particles having a particle size of 10 to 150 µM and the anionic surfactant is used, and the monomer aqueous solution has a temperature of 30 to 60° C.

6. The method for preparing a super absorbent polymer according to claim 5, wherein the monomer aqueous solution further comprises an additive selected from the group consisting of a polyvalent metal salt, a photoinitiator, a thermal initiator, a polyalkylene glycol-based polymer, and any combination thereof.

7. The method for preparing a super absorbent polymer according to claim 6, wherein the additive is used in an amount of 2000 ppmw or less, based on 100 parts by weight of the water-soluble ethylenically unsaturated monomer.

8. The method for preparing a super absorbent polymer according to claim 1, wherein the super absorbent polymer has a centrifuge retention capacity (CRC) measured according to EDANA test method No. WSP 241.3 of 28 to 35 g/g, and an absorbency under load (AUL) at 0.9 psi measured according to EDANA test method No. WSP 242.3 of 16 to 23 g/g.

* * * * *